United States Patent [19]

Nakasima et al.

[11] Patent Number: 5,260,322

[45] Date of Patent: Nov. 9, 1993

[54] ANGIOTENSION II ANTAGONISTS IN THE TREATMENT OF HYPERURICEMIA

[75] Inventors: Mitsuyosi Nakasima, Hamamatsu; Ikuo Ohta, Tama; Mitsutaka Kanamaru, Hamamatsu; Kazuo Kamei, Yokohama, all of Japan

[73] Assignee: Merck & Co., Inc., Rahway, N.J.

[21] Appl. No.: 771,067

[22] Filed: Oct. 1, 1991

[30] Foreign Application Priority Data

Oct. 8, 1990 [JP] Japan ................... 2-270214

[51] Int. Cl.$^5$ ............ A61K 31/44; A61K 31/41; A61K 31/415
[52] U.S. Cl. .................... 514/341; 514/381; 514/384; 514/396; 514/397; 514/383
[58] Field of Search ............ 514/341, 381, 397, 383, 514/384, 396

[56] References Cited

PUBLICATIONS

Wong et al., *J. Pharmacol & Exp. Ther.*, 252, 726–732 (1990).
Johnson et al., *Drug News & Perspectives*, 3, 337–351 (1990).
Ferris et al., *Amer. J. Med.* 44, 359–365 (1968).
Saito et al., *J. Amer. Geriatric Soc.* 26, 241–247 (1978).
Chiu et al., *Biochem & Biophys. Res. Comm.* 165, 196–203 (1989).
Koepke et al., *Hypertension*, 15, 841–847 (1990).
Wessesls et al., *Medizinische Klinik*, 69, 599–606 (1974).

*Primary Examiner*—Leonard Schenkman
*Assistant Examiner*—Kimberly R. Jordan
*Attorney, Agent, or Firm*—Robert J. North; William H. Nicholson; Joseph F. DiPrima

[57] ABSTRACT

A pharmaceutical composition comprising a non-peptide type angiotension II receptor antagonist is useful for the treatment of hyperuricemia.

12 Claims, No Drawings

ANGIOTENSION II ANTAGONISTS IN THE TREATMENT OF HYPERURICEMIA

BACKGROUND OF THE INVENTION

It is considered that when uric acid content in blood exceeds a certain limit, uric acid would deposit as sodium urate and deposition of sodium urate on the articular cavity or kidney would cause gout, renal disorders or vascular disorders. As known causes of hyperuricemia, there are reduced excretion of uric acid, excessive production of uric acid, abnormality of purine metabolizing enzyme, disease associated with hematopoietic organ or renal disorders, administration of chemicals such as pyrazinamide or thiazide, and the like. Irrespective of any cause, continuous hyperuricemia results in incidence of gout in most cases and if further worsened, leads to renal insufficiency or cardiovascular disorders. Further in the case of children, a disease called Lesch-Nyhan syndrome which is caused by excessive production of uric acid due to enzyme abnormality is known.

Since these diseases are caused by high blood concentration of uric acid, drugs having an activity of excreting uric acid, for example, probenecid, sulfinpyrazone or benzbromarone have been used for the treatment of hyperuricemia.

The present invention provides compounds having excellent properties as agents for the treatment of hyperuricemia.

DETAILED DESCRIPTION OF THE INVENTION

As a result of extensive investigations to solve the foregoing problems, the present inventors have found that a series of non-peptide type compounds having an angiotension II receptor-antagonizing activity are useful for the prevention or treatment of hyperuricemia. The present invention has thus been accomplished.

That is, the present invention relates to compositions for the prevention or treatment of hyperuricemia comprising a non-peptide type compound having an angiotensin II receptor-antagonizing activity.

The non-peptide type angiotensin II receptor antagonists which are used in the present invention may be any compounds as long as they are compounds which do not fall under the category of compounds formed by binding two or more amino acids through peptide bond (—COHN—) and have an antagonizing activity against angiotensin II receptor. As non-peptide type compounds having such an action of antagonizing an angiotensin II receptor, compounds described in, for example, the following publications, may be given:

(a) Andrew T. Chiu et al. The Journal of Pharmacology and Experimental Therapeutics, 247, 1-7 (1988)

(b) Andrew T. Chiu et al. European Journal of Pharmacology, 157, 13-21 (1988)

(c) Andrew T. Chiu et al. European Journal of Pharmacology, 170, 117-118 (1989)

(d) Pancras C. Wong et al. Hypertenion, 13, 489-497 (1989)

(e) Andrew T. Chiu et al. Biochemical and Biophysical Research Communications, 165, 196-203 (1989)

(f) Pancras C. Wong et al. The Journal of Pharmacology and Experimental Therapeutics, 250, 515-522 (1989)

(g) Andrew T. Chiu et al. The Journal of Pharmacology and Experimental Therapeutics, 250, 867-874 (1989)

(h) Andrew T. Chiu et al. The Journal of Pharmacology and Experimental Therapeutics, 252, 711-718 (1990)

(i) John O. Koepke et al. Hypertenion, 15, 841-847 (1990)

(j) Edwin K. Jackson et al. Life Science, 46, 945-953 (1990)

(k) John V. Duncia et al. Journal of Medical Chemistry, 33, 1312-1329 (1990)

(l) David J. Carini et al. Journal of Medical Chemistry, 33, 1330-1336 (1990)

(m) Pancras C. Wong et al. Hypertension, 15, 823-833 (1990)

(n) R. S. L. Chang et al. Molecular Pharmacology, 29, 347-351 (1990)

(o) Alexander L. Johnson et al. Drug News and Perspectives, 3, 337-351 (1990).

In addition, compounds disclosed in the following patents may also be given as examples of the non-peptide type compounds having an angiotensin II receptor-antagonizing activity which can be used in the present invention.

(1) Japanese Patent Application Laid-Open No. 54-148,788

(2) Japanese Patent Application Laid-Open No. 56-71,073

(3) Japanese Patent Application Laid-Open No. 56-71,074

(4) Japanese Patent Application Laid-Open No. 57-98,270

(5) Japanese Patent Application Laid-Open No. 58-157,768

(6) Japanese Patent Application Laid-Open No. 62-240,683

(7) Japanese Patent Application Laid-Open No. 63-23,868

(8) Japanese Patent Application Laid-Open No. 1-287,071

(9) European Patent Laid-Open No. 324,377

(10) U.S. Pat. No. 4,880,804

(11) U.S. Pat. No. 4,916,129

(12) Japanese Patent Application No. 2-138,653.

Among the compounds disclosed in the patents supra or described in the publications supra, a group of preferred compounds and preferred examples are shown below.

A group of compounds preferred as the non-peptide type compounds having an angiotensin II receptor-antagonizing activity which are the effective ingredient of the composition for the prevention or treatment of hyperuricemia are represented by general formula (I) below.

(wherein each of $Z^1$, $Z^2$, and $Z^3$, independently represents:

nitrogen atom, a group represented by general formula: $=C(X^2)-$ or, a group represented by general formula: $=C(X^3)-$;
each of $X^1$, $X^2$, and $X^3$ independently represents:
hydrogen,
hydroxy,
mercapto,
halogen,
formyl,
carboxyl,
carbamoyl,
methoxycarbonyl,
ethoxycarbonyl,
an alkyl group having 1 to 10 carbon atoms (wherein the alkyl group may be substituted with a substituent selected from the group consisting of hydroxy, methoxy, ethoxy, halogen, carboxyl, methoxycarbonyl, ethoxycarbonyl, methoxycarbonylamino, cyano, carbamoyl, acetoxy, acetamido, mercapto, methylthio, ethylthio, phenyl and tetrazolyl,
an alkyl group having 2 to 5 carbon atoms (wherein the alkenyl group may be substituted with a substituent selected from the group consisting of hydroxy, methoxy, ethoxy, carboxyl, methoxycarbonyl and ethoxycarbonyl, alkynyl having 2 to 5 carbon atoms, cycloalkyl having 3 to 6 carbon atoms, alkoxy having 1 to 4 carbon atoms, alkylthio having 1 to 4 carbon atoms, thienyl, or phenyl (wherein the phenyl may be substituted with 1 to 3 substituents selected from the group consisting of hydroxy, halogen, methoxy, ethoxy, n-propoxy, n-butoxy, mercapto, methylthio, ethylthio, n-propylthio, n-butylthio, methyl, ethyl, n-propyl, isopropyl, n-butyl, nitro, amino, methylamino, dimethylamino, ethylamino, diethylamino, n-propylamino, n-butylamino, phenyl, phenoxy, benzyl, benzyloxy, carboxyl, methoxycarbonyl, ethoxycarbonyl and carbamoyl;
when $Z^2$ and $Z^3$ represent a group of general formula: $=C(X^2)-$ or a group of general formula: $=C(X^3)-$, $X^2$ and $X^3$ may be combined together to form:
A group represented by general formula:

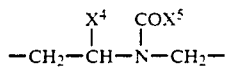

(wherein $X^4$ represents carboxyl, carbamoyl, formyl, cyano or hydroxymethyl, and $X^5$ represents fluorenyl, phenyl(methyl)amino, cyclopropylmethyl, cyclopentylmethyl, cyclohexylmethyl, cyclohexyl(phenyl)methyl or benzhydryl:
(wherein the phenyl in benzhydryl may be substituted with a substituent selected from the group consisting of halogen, hydroxy, methoxy, ethoxy, mercapto, methylthio, ethylthio, amino, methylamino, dimethylamino, ethylamino, diethylamino, methyl and ethyl));
a group represented by general formula:

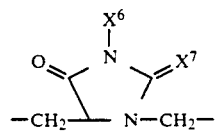

(wherein $X^6$ represents alkyl having 1 to 4 carbon atoms or phenyl:
(wherein the phenyl may be substituted with 1 or 2 substituents selected from the group consisting of halogen, methyl, ethyl, hydroxy, methoxy, ethoxy, mercapto, methylthio, ethylthio, amino, methylamino, dimethylamino, ethylamino and diethylamino; and $X^7$ represents an oxygen atom or sulfur atom);
a group represented by general formula:

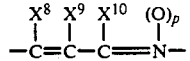

(wherein each of $X^8$, $X^9$ and $X^{10}$ independently represents hydrogen, alkyl of 1 to 6 carbon atoms):
(wherein the alkyl group may be substituted with hydroxy, amino, mercapto, methoxy, methylthio, carboxyl, carbamoyl, acetylamino or acetoxy); alkoxycarbonyl group having 2 to 5 carbon atoms, halogen, cyano, carboxyl, carbamoyl, acetyl, amino, mono- or dialkylamino having 1 to 6 carbon atoms which may be substituted with an amino, pyrrolidinyl, piperidino, piperazino, morpholino, thiomorpholino, triazolyl, tetrazolyl, trichloromethyl, tribromomethyl, trifluoromethyl or phenyl (wherein the phenyl may be substituted with methyl, ethyl, methoxy, ethoxy, hydroxy, methylthio, ethylthio, mercapto, carboxyl and cyano); and p represents 0 or 1); a group represented by general formula:

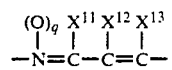

(wherein each of $X^{11}$, $X^{12}$, and $X^{13}$ independently has the same significance as $X^8$, $X^9$ or $X^{10}$, and q has the same significance as p);
a group represented by general formula:

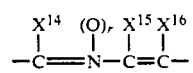

(wherein each of $X^{14}$, $X^{15}$ and $X^{16}$ independently has the same significance as $X^8$, $X^9$ of $X^{10}$, and r has the same significance as p);
a group represented by general formula:

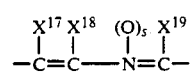

(wherein each of $X^{17}$, $X^{18}$ and $X^{19}$ independently has the same significance as $X^8$, $X^9$ or $X^{10}$, and s has the same significance as p);
a group represented by general formula:

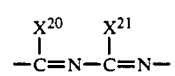

(wherein each of $X^{20}$ and $X^{21}$ independently has the same significance as $X^8$, $X^9$ or $X^{10}$);
a group represented by general formula:

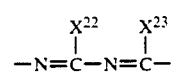

(wherein each of $X^{22}$ and $X^{23}$ independently has the same significance as $X^8$, $X^9$ or $X^{10}$);
a group represented by general formula:

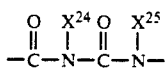

(wherein each of $X^{24}$ and $X^{25}$ independently represents hydrogen or alkyl of 1 to 4 carbon atoms (wherein the alkyl group may be substituted with a substituent selected from the group consisting of hydroxy, methoxy, ethoxy, methoxycarbonyl, carboxyl, ethoxycarbonyl and carbamoyl));
a group represented by general formula:

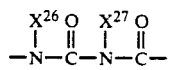

(wherein each of $X^{26}$ and $X^{27}$ independently has the same significance as $X^{24}$ and $X^{25}$); or,
a group represented by general formula:

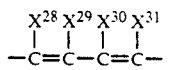

(wherein each of $X^{28}$, $X^{29}$, $X^{30}$ and $X^{31}$ independently represents hydrogen, an alkyl group having 1 to 4 carbon atoms (wherein the alkyl group may be substituted with a substituent selected from the group consisting of hydroxy, methoxy, ethoxy, carboxyl, methoxycarbonyl, ethoxycarbonyl, carbamoyl, acetyl, acetoxy, acetamido and halogen), halogen, a perfluoroalkyl group having 1 to 6 carbon atoms, carboxyl, carbamoyl, cyano, formyl, methoxy, ethoxy, propoxy, methoxycarbonyl or ethoxycarbonyl);
Y represents:
phenethyl,
cyclohexylethyl,
adamantylethyl,
or a group represented by general formula:

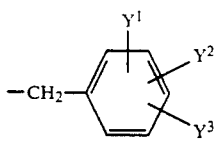

(wherein each of $Y^1$ and $Y^2$ independently represents:
hydrogen,
halogen,
nitro,
carboxyl,
amino,
cyano,
formyl,
hydroxyiminomethyl,
trifluoromethylsulfonylamino,
trifluoroacetylamino,
an alkoxy group having 1 to 4 carbon atoms,
an alkyl group having 1 to 4 carbon atoms,
carboxymethyl, tetrazolylmethyl,
a group represented by formula:

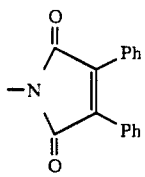

a group represented by general formula:

—NHCO(CH$_2$)$_t$COOH (wherein t represents 1 to 3):
a group represented by formula:

—NHCOCH=CH—CO$_2$H;

a group represented by formula:

—NHCOCH$_2$CH(Ph)CO$_2$H;

a group represented by formula:

—NHCOCH(Ph)CH$_2$CO$_2$H;

a group represented by formula

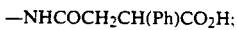

a group represented by formula:

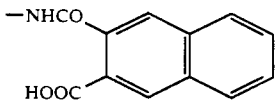

a group represented by formula:

—CONHCH(Ph)CO$_2$H;

a group represented by formula:

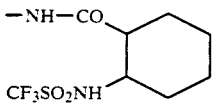

a group represented by formula:

—NHCOC(Ph)=C(Ph)CO$_2$H;

phthalimido;
benzyloxy;
a mono- or dialkylamino having 1 to 4 carbon atoms;
acetoxy; or,
propionyloxy;
$Y^3$ represents:
hydrogen; or,
a group represented by general formula:

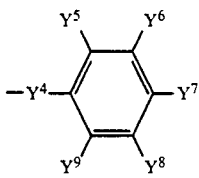

(wherein $Y^4$ represents a single bond; oxygen; sulfur; carbonyl;

a group of formula: —NH—;

a group of formula: —CH=CH— a group of general formula: —N($Y^{10}$)CO—

(wherein $Y^{10}$ represents hydrogen, methyl or phenyl);

a group of general formula: —CON($Y^{11}$)—

(wherein $Y^{11}$ represents hydrogen, methyl or phenyl);

a group of formula: —CH$_2$HH—;

a group of formula: —NHCH$_2$—;

a group of general formula: —CH$_2$—$Y^{12}$—

(wherein $Y^{12}$ represents oxygen or sulfur); a group of general formula: —$Y^{13}$—CH$_2$—

(wherein $Y^{13}$ represents oxygen or sulfur); or a group of formula: —NHCONH—;

each of $Y^5$, $Y^6$, $Y^7$, $Y^8$ and $Y^9$ independently represents an alkyl group having 1 to 4 carbon atoms, halogen, carboxyl, carbamoyl, hydroxy, methoxy, ethoxy, mercapto, methylthio, ethylthio, sulfo, sulfamoyl, nitro, trifluoromethanesulfonylamino, methanesulfonylamino, benzenesulfonylamino, 4-chlorobenzenesulfonylamino, acetylaminosulfonylmethyl, methoxycarbonyl, ethoxycarbonyl, propyloxycarbonyl, amino, formyl, phospho, phosphono or cyano).

Herein, terms used in the description on the group of preferred compounds are specifically explained.

The halogen atom refers to fluorine atom, chlorine atom, bromine atom or iodine atom.

The alkyl group having 1 to 10 carbon atoms refers to a straight or branched alkyl group having 1 to 10 carbon atoms, for example, methyl, ethyl, n-propyl, isopropyl, n-butyl, isobutyl, tert-butyl, n-pentyl, isopentyl, n-hexyl, isohexyl, n-heptyl, n-octyl, n-nonyl, n-decanyl or the like.

The alkenyl group having 2 to 5 carbon atoms refers to straight or branched alkenyl group having 2 to 5 carbon atoms, for example, vinyl, 1-methylvinyl, 1-propenyl, 2-methylpropenyl, 1-butenyl, 2-butenyl, 3-butenyl, 1-pentenyl, 2-pentenyl, 3-pentenyl, 4-pentenyl, 3-methyl-1-butenyl, 3-methyl-2-pentenyl, or the like.

The alkynyl group having 2 to 5 carbon atoms refers to a straight or branched alkynyl group having 2 to 5 carbon atoms, for example, ethynyl, 1-propynyl, 2-propynyl, 1-butynyl, 2-butynyl, 3-butynyl, 3-methyl-1-propynyl, 3-methylbutynyl, 1-pentynyl, 2-pentynyl, 3-pentynyl, 4-pentynyl, or the like.

The alkoxy group having 1 to 4 carbon atoms refers to an alkoxy group, for example, methoxy, ethoxy, n-propoxy, isopropoxy, n-butoxy, isobutoxy, tert-butoxy, or the like.

The alkylthio group having 1 to 4 carbon atoms refers to an alkylthio group, for example, methylthio, ethylthio, n-propylthio, isopropylthio, n-butylthio, isobutylthio, tert-butylthio, or the like.

The alkyl group having 1 to 6 carbon atoms refers to a straight or branched alkyl group having 1 to 6 carbon atoms, for example, methyl, ethyl, n-propyl, isopropyl, n-butyl, isobutyl, tert-butyl, n-pentyl, isopentyl, n-hexyl or the like.

The mono- or dialkylamino group having 1 to 6 carbon atoms refers to a mono- or dialkylamino group, for example, methylamino, ethylamino, n-propylamino, n-butylamino, isobutylamino, n-pentylamino, n-hexylamino, dimethylamino, diethylamino, dipropylamino, or the like.

The perfluoroalkyl group having 1 to 6 carbon atoms refers to an alkyl group wherein hydrogen atoms in a straight or branched alkyl group having 1 to 6 carbon atoms are all substituted with fluorine atoms and is shown by, for example, formulae: $CF_3$, $CF_2CF_3$, $CF_2CF_2CF_3$, $CF(CF_3)_2$, $CF_2CF_2CF_2CF_3'$, $CF_2CF(CF_3)_2$, $CF_2CF_2CF_2CF_2CF_3$, $CF_2CF_2CF_2CF_2CF_3$ or $CF_2CF_2CF(CF_3)_2$, or the like.

The alkyl group having 1 to 4 carbon atoms refers to a straight or branched alkyl group having 1 to 4 carbon atoms, for example, methyl, ethyl, n-propyl, isopropyl, n-butyl, isobutyl, or the like.

The alkoxycarbonyl group having 2 to 5 carbon atoms refers to an alkyl ester having 2 to 5 carbon atoms, for example, methoxycarbonyl group, ethoxycarbonyl group, n-propoxycarbonyl group, isopropoxycarbonyl group, n-butoxycarbonyl group, isobutoxycarbonyl group, tert-butoxycarbonyl group, or the like.

As the pharmaceutically acceptable non-toxic salts of the non-peptide type compounds for the prevention or treatment of hyperuricemia having an angiotensin II receptor-antagonizing activity, any salts may be used as long as they are acceptable as drugs. Examples of the salts include salts with inorganic or organic bases such as ammonium salt, sodium salt, potassium salt, magnesium salt, triethylamine salt, dicyclohexylamine salt, N-methylglucamine salt, or the like; salts with amino acids such as arginine, lysine, or the like; salts with inorganic or organic acids such as hydrochloride, hydrobromide, sulfate, phophate, methanesulfonate, toluenesulfonate, maleate, fumarate, camphorsulfonate, or the like.

Next, preferred examples of the non-peptide type compounds having an angiotensin II receptor-antagonizing activity in accordance with the present invention are shown in Tables 1 through 10.

| No. | $R^1$ | $R^2$ | $R^3$ | $R^4$ | $R^5$ | $A^1$ | $R^6$ | $R^7$ | $R^8$ | $R^9$ | $R^{10}$ |
|---|---|---|---|---|---|---|---|---|---|---|---|
| 1 | n-Bu | Cl | CH₂CO₂Me | H | H | —NHCO— | CO₂Na | H | H | H | H |
| 2 | " | " | (CH₂)₂CO₂Me | " | " | " | CO₂H | " | " | " | " |
| 3 | " | " | CH₂CO₂Me | " | " | " | —NSO₂CF₃ Na | " | " | " | " |
| 4 | " | " | CH₂CO₂H | " | " | single bond | CO₂H | " | " | " | " |
| 5 | " | " | CO₂H | " | " | " | " | " | " | " | " |
| 6 | " | " | CHO | " | " | " | " | " | " | " | " |
| 7 | Et—CH=CH | " | CHO | " | " | " | " | " | " | " | " |
| 8 | " | " | CH₂OH | " | " | " | Tet.K | " | " | " | " |
| 9 | n-Bu | " | CHO | " | " | " | H | " | " | " | " |
| 10 | " | " | CH₂OH | " | " | " | " | " | " | " | " |
| 11 | " | " | (CH₂)₂CO₂H | " | " | " | CO₂H | CO₂H | H | " | " |
| 12 | " | " | CH₂OH | " | " | " | CONH₂ | H | CO₂H | " | " |
| 13 | " | " | CH₂OMe | " | " | " | H | " | " | " | " |
| 14 | " | " | CH₂OH | " | " | " | CO₂Na | " | " | " | " |
| 15 | " | " | " | " | " | " | " | " | " | " | " |
| 16 | " | " | (CH₂)₂—Tet | " | " | —NHCO— | " | " | " | " | " |
| 17 | " | " | CH₂CO₂Na | " | " | " | " | " | " | " | " |
| 18 | " | " | CH₂CO₂Me | " | " | " | " | " | " | " | " |
| 19 | (CH₃)₂C=CH (H,Et) | " | CH₂OH | " | " | single bond | CO₂H | " | " | " | " |
| 20 | n-Bu | Cl | CH₂OH | H | H | —OCH₂— | CO₂H | H | H | H | H |
| 21 | n-Bu | " | " | " | " | —O— | " | " | " | " | " |
| 22 | " | " | " | " | " | —S— | " | " | " | " | " |
| 23 | " | " | " | " | " | —NH— | " | " | " | " | " |
| 24 | " | " | " | " | " | —CO— | " | " | " | " | " |
| 25 | " | " | " | " | " | single bond | " | " | " | " | " |
| 26 | (Et)(H)C=C(H)— | " | " | " | " | " | " | " | " | " | " |

-continued

[Structure shown: compound with R¹-C(=N)-N-CH2-phenyl group bearing R⁴,R⁵,R⁶ on one ring and A¹ linking to another phenyl with R⁷,R⁸,R⁹,R¹⁰; R² and R³ on the vinyl carbon]

| No. | R¹ | R² | R³ | R⁴ | R⁵ | R⁶ | A¹ | R⁷ | R⁸ | R⁹ | R¹⁰ |
|---|---|---|---|---|---|---|---|---|---|---|---|
| 27 | n-Pr | " | " | " | " | " | " | " | " | " | " |
| 28 | n-Bu | " | " | " | " | " | " | " | " | " | " |
| 29 | n-Pen | " | " | " | " | " | " | " | " | " | " |
| 30 | Et | " | " | " | " | " | " | " | " | " | " |
| 31 | H₂C=CH–n-Pr (H\C=C/H, n-Pr) | " | " | " | " | " | " | " | " | " | " |
| 32 | n-Bu–S– | " | " | " | " | " | " | " | " | " | " |
| 33 | H\C=C/H (CHMe-OH) | " | " | " | " | " | " | " | " | " | " |
| 34 | Ph | " | " | " | " | " | " | " | " | " | " |
| 35 | CH₂OH | " | " | " | " | " | " | " | " | " | " |
| 36 | –CHF–n-Pr | " | " | " | " | " | " | " | " | " | " |
| 37 | n-Bu | " | " | " | " | " | H\C=C/H | " | " | " | " |
| 38 | " | " | CH₂CO₂Me | " | " | " | —NHCONH— | " | " | " | " |
| 39 | " | " | " | " | " | Tet | single bond | " | " | " | " |
| 40 | " | " | " | " | " | Me | —NHCO— | " | " | " | " |
| 41 | " | " | " | " | " | H | —NHCH₂— | " | " | " | " |

-continued

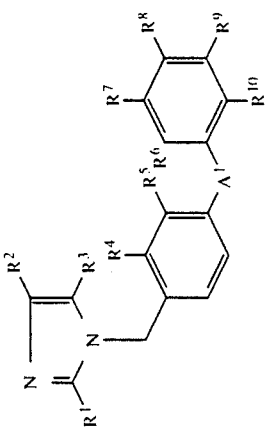

| No. | R¹ | R² | R³ | R⁴ | R⁵ | A¹ | R⁶ | R⁷ | R⁸ | R⁹ | R¹⁰ |
|---|---|---|---|---|---|---|---|---|---|---|---|
| 42 | " | CH₂COOMe | " | " | " | —NHCO— | CO₂H | " | " | " | " |
| 43 | " | Cl | Cl | " | " | " | " | " | " | " | " |
| 44 | " | " | CH₂OMe | " | " | " | " | " | " | " | " |
| 45 | " | " | CH₂CO₂Me | " | " | " | " | " | " | F | F |
| 46 | n-Bu | Cl | " | " | " | " | " | F | H | Me | H |
| 47 | " | " | CH₂CO₂Me | H | H | " | CO₂H | H | Me | H | H |
| 48 | " | " | " | " | " | " | " | H | H | NO₂ | NO₂ |
| 49 | " | " | " | " | " | " | " | " | NO₂ | H | OMe |
| 50 | " | " | " | " | " | " | " | " | H | " | Me |
| 51 | " | " | " | " | " | " | " | " | " | " | Cl |
| 52 | " | " | " | " | " | " | " | Cl | " | " | " |
| 53 | " | " | " | " | " | " | " | " | " | " | " |
| 54 | " | " | CH₂OMe | " | " | " | " | " | " | " | " |
| 55 | " | " | " | " | " | —NCO—<br>\|<br>Me | O—CP | H | " | " | H |
| 56 | " | " | CH₂CO₂Me | " | " | —NHCO— | CF₃SO₂N | " | " | " | " |
| 57 | " | " | " | " | " | " | H | " | " | " | " |
| 58 | " | " | " | " | " | —NCO—<br>\|<br>Ph | MeSO₂N | " | " | " | " |
| 59 | " | " | " | " | " | —NHCO— | H | " | " | " | " |
| 60 | " | " | " | " | " | " | CF₃SO₂N | " | " | Cl | " |
| 61 | " | " | " | " | " | " | " | " | " | Br | " |
| 82 | " | " | " | " | " | " | " | " | " | I | " |
| 63 | " | " | " | " | " | " | " | " | " | Me | " |
| 64 | " | " | " | " | " | " | " | Me | " | H | " |

-continued

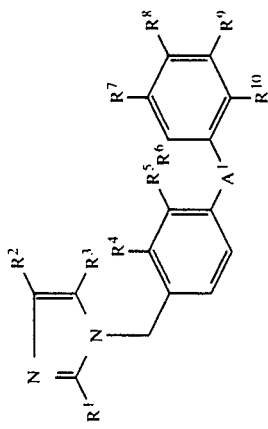

| No. | R¹ | R² | R³ | R⁴ | R⁵ | A¹ | R⁶ | R⁷ | R⁸ | R⁹ | R¹⁰ |
|---|---|---|---|---|---|---|---|---|---|---|---|
| 65 | " | " | " | " | " | " | H | H | NO₂ | " | " |
| 66 | " | " | " | " | " | " | HO₂S | NO₂ | Cl | NO₂ | " |
| 67 | " | " | CH₂OMe | " | " | " | H | H | H | H | " |
| 68 | " | " | CH₂CO₂Me | " | " | " | " | " | " | " | " |
| 69 | " | " | " | " | " | " | CO₂H | CF₃SO₂NH | CF₃SO₂NH | " | " |
| 70 | " | " | " | " | " | " | CO₂H | H | H | " | " |
| 71 | H | H | H | " | " | —NHCO— | CO₂H | H | H | H | H |
| 72 | Me | " | H | " | " | " | " | " | " | " | " |
| 73 | Et | H | H | H | " | " | " | " | " | " | " |
| 74 | n-Pr | " | " | " | " | " | " | " | " | " | " |
| 75 | n-Bu | " | " | " | " | " | " | " | " | " | " |
| 76 | n-Pen | " | " | " | " | " | " | " | " | " | " |
| 77 | n-Hex | " | " | " | " | " | " | " | " | " | " |
| 78 | n-Hep | " | " | " | " | " | " | " | " | " | " |
| 79 | Ph(CH₂)₂ | " | " | " | " | " | " | " | " | " | " |
| 80 | p-MP | " | " | " | " | " | " | " | " | " | " |
| 81 | c-Hex | " | " | " | " | " | " | " | " | " | " |
| 82 | i-Pr | H | CH₂OH | " | " | " | Tet | " | " | " | " |
| 83 | H | Cl | " | " | " | " | CO₂H | " | " | " | " |
| 84 | Ph(CH₂)₃ | H | OMe | " | " | " | H | Me | H | " | " |
| 85 | n-Bu | Cl | " | " | " | —CONH— | " | H | " | " | " |
| 86 | " | " | CH₂CO₂Me | " | " | " | CO₂H | CO₂Me | " | " | " |
| 87 | " | " | CH₂OH | " | " | —NHCO— | H | CO₂H | " | " | " |
| 88 | " | " | " | " | " | single bond | CO₂H | H | " | " | " |
| 89 | " | " | " | " | " | —OCH₂— | H | " | " | " | " |
| 90 | " | " | CO₂Et | " | " | " | CO₂H | " | " | " | " |
| 91 | n-Pr-S | H | CH₂OH | " | " | " | H | " | " | " | " |
| 92 | " | " | " | " | " | —CO— | CO₂H | " | " | " | " |
| 93 | n-Bu | Cl | CH₂OMe | " | " | " | CO₂Me | " | " | " | " |
| 94 | " | " | " | " | " | " | CO₂H | " | " | " | " |

-continued

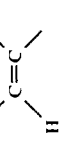

| No. | R¹ | R² | R³ | R⁴ | R⁵ | A¹ | R⁶ | R⁷ | R⁸ | R⁹ | R¹⁰ |
|---|---|---|---|---|---|---|---|---|---|---|---|
| 98 | " | " | CH₂OH | " | " | CH=C(Me)(H) | CN | " | " | " | " |
| 99 | n-Bu | Cl | CH₂OH | H | H | CH=C(Me)(H) | CO₂H | H | H | H | H |
| 100 | " | " | CH₂OMe | " | " | —NHCONH— | NO₂ | " | " | " | " |
| 101 | " | " | " | " | " | " | NH₂ | " | " | " | " |
| 102 | " | " | " | " | " | " | CF₃SO₂N(H) | " | " | " | " |
| 103 | " | " | CH₂CO₂Me | " | " | —NHCO— | CO₂H | " | " | " | " |
| 104 | " | H | CH₂OH | " | " | single bond | H | " | " | " | " |
| 105 | " | Cl | " | " | " | " | " | CO₂H | " | " | " |
| 106 | " | " | CH₂CO₂Me | " | " | —CO— | CO₂H | " | " | " | " |
| 107 | " | " | CH₂OMe | " | " | " | " | " | " | " | " |
| 108 | " | " | CH₂OH | " | " | " | " | " | " | " | " |
| 109 | " | CH₂OH | Cl | " | " | " | " | " | " | " | " |
| 110 | " | CH₂OCOMe | " | " | " | " | " | " | " | " | " |
| 111 | " | Cl | CH₂NHCO₂Me | " | " | " | " | " | " | " | " |
| 112 | " | " | CH₂OMe | " | " | —O— | " | " | " | " | " |
| 113 | " | " | CH₂OH | " | " | —S— | " | " | " | " | " |
| 114 | " | " | " | " | " | —OCH₂— | " | " | " | " | " |
| 115 | " | H | CH₂OCOMe | " | " | " | " | " | " | " | " |
| 116 | " | Cl | CH₂OMe | " | " | " | " | " | " | " | " |
| 117 | " | H | CH₂OH | " | " | " | " | " | " | " | " |
| 118 | n-Pr—S | Cl | CH₂OMe | " | " | " | " | " | " | " | " |
| 119 | EtS | H | CH₂OH | " | " | " | " | " | " | " | " |

TABLE 2

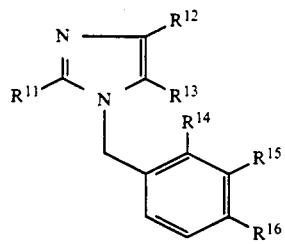

| No. | R¹¹ | R¹² | R¹³ | R¹⁴ | R¹⁵ | R¹⁶ |
|---|---|---|---|---|---|---|
| 120 | n-Bu | Cl | CH₂CO₂Na | Cl | H | H |
| 121 | " | " | " | NO₂ | " | " |
| 122 | " | " | " | H | " | CO₂Na |
| 123 | " | " | CH₂CO₂H | NO₂ | " | H |
| 124 | " | " | CH₂CO₂Na | NO₂ | " | " |
| 125 | " | " | CH₂CO₂H | H | " | NO₂ |
| 126 | " | " | CH₂CO₂Me | NO₂ | " | H |
| 127 | " | " | CH₂CO₂H | H | " | NH₂ |
| 128 | " | " | CH₂CO₂Na | " | " | CO₂Na |
| 129 | " | " | " | " | " | H |
| 130 | " | " | " | Me | OMe | " |
| 131 | " | " | CH₂CO₂Me | NO₂ | H | " |
| 132 | " | " | CH₂CO₂H | H | " | " |
| 133 | " | " | " | Cl | " | " |
| 134 | " | " | " | " | " | CO₂H |
| 135 | " | " | CH₂CO₂Me | H | " | NH₂ |
| 136 | " | " | CH₂OMe | " | " | " |
| 137 | " | " | CH₂OH | " | " | " |
| 138 | " | CH₂CO₂H | Cl | " | " | CO₂H |
| 139 | " | Cl | CH₂OH | " | " | " |
| 140 | " | CH₂OH | Cl | " | " | " |
| 141 | n-Bu | Cl | CH₂CO₂Me | H | H | CO₂H |
| 142 | " | " | CH₂CO₂H | " | " | CH₂CO₂H |
| 143 | " | " | CH₂COOMe | " | " | NO₂ |
| 144 | " | " | CH₂CO₂H | " | " | CHO |
| 145 | " | " | " | " | " | CH=NOH |
| 146 | " | " | " | " | " | OMe |
| 147 | " | " | CH₂COOMe | " | " | 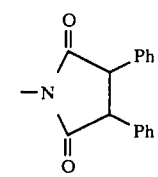 |
| 148 | " | " | " | " | " | NHCO(CH₂)₂CO₂H |
| 149 | " | " | " | " | " | NHCO(CH₂)₃CO₂H |
| 150 | " | " | " | " | " | 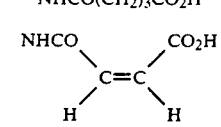 |
| 151 | " | " | CH₂OCH₃ | " | " | NHCOCH₂CHCO₂H<br>              Ph |
| 152 | " | " | " | " | " | NHCOCHCH₂CO₂H<br>           Ph |
| 153 | " | " | CH₂CO₂Me | " | " | 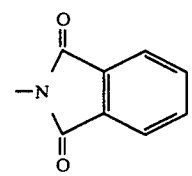 |
| 154 | " | " | " | " | " | 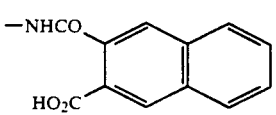 |

TABLE 2-continued

Structure: imidazole with R11 at 2-position, R12 at 4-position (=), R13 at 5-position, N-CH2-phenyl with R14 (ortho), R15 (meta), R16 (para)

| No. | R11 | R12 | R13 | R14 | R15 | R16 |
|---|---|---|---|---|---|---|
| 155 | " | " | " | " | " | NHSO₂CF₃ |
| 156 | " | " | " | " | " | NHCOCF₃ |
| 157 | " | " | —CH₂—Tet | " | " | —CH₂—Tet |
| 158 | " | " | CH₂CO₂Me | " | " | —NHCO-(2-(CF₃SO₂NH)cyclohexyl) |
| 159 | " | " | CH₂CO₂H | " | CO₂H | H |
| 160 | " | " | " | CO₂H | H | " |
| 161 | " | " | CH₂—Tet | H | CH₂—Tet | " |
| 162 | " | " | CH₂CO₂Me | —NHCO-(2-HO₂C-phenyl) | H | " |
| 163 | " | " | " | —NHCO-(2-(CF₃SO₂NH)-phenyl) | " | " |
| 164 | n-Bu | Cl | OMe | H | H | CO—L—Phe |
| 165 | " | " | " | " | " | CO—D—Phe |
| 166 | " | " | " | " | " | CO—L—Pro |
| 167 | " | " | " | " | " | —CO—D—Pro |
| 168 | " | " | CH₂OH | " | " | NO₂ |
| 169 | " | " | " | " | NO₂ | H |
| 170 | " | " | " | NO₂ | H | " |
| 171 | " | " | " | H | " | CN |
| 172 | " | " | " | " | CN | H |
| 173 | " | " | " | CN | H | " |
| 174 | " | CH₂OH | Cl | H | " | NO₂ |
| 175 | " | " | " | " | NO₂ | H |
| 176 | " | " | " | NO₂ | H | " |
| 177 | " | " | " | H | " | CN |
| 178 | " | " | " | " | CN | H |
| 179 | " | " | " | CN | H | " |
| 180 | " | " | " | H | " | CHO |
| 181 | " | " | " | " | " | OMe |
| 182 | " | Cl | CH₂CN | " | " | NO₂ |
| 183 | " | " | " | " | NO₂ | H |
| 184 | " | " | " | NO₂ | H | " |
| 185 | " | " | " | H | " | CN |
| 186 | " | " | " | " | CN | H |
| 187 | n-Bu | Cl | CH₂COOH | H | H | NO₂ |
| 188 | " | " | " | " | NO₂ | H |
| 189 | " | " | " | NO₂ | H | " |
| 190 | " | " | CH₂OMe | H | " | NO₂ |
| 191 | " | " | CH₂CO₂Me | " | NO₂ | H |
| 192 | " | " | " | NH₂ | H | " |
| 193 | " | " | CH₂OCH₃ | H | " | NHMe |
| 194 | " | " | CH₂CO₂Me | —NHCOC(Ph)=C(Ph)—CO₂H | " | H |
| 195 | " | " | " | H | —NHCOC(Ph)=C(Ph)—CO₂H | " |

TABLE 2-continued

Structure: Imidazole with R11 at 2-position, R12 at 5-position, R13 at 4-position, N-CH2-phenyl where phenyl has R14 (ortho), R15 (meta), R16 (para).

| No. | R11 | R12 | R13 | R14 | R15 | R16 |
|-----|-----|-----|-----|-----|-----|-----|
| 196 | " | " | " | " | H | —NHCOC(Ph)=C(Ph)—CO2H |
| 197 | " | " | CH2OMe | —NHCOC(Ph)=C(Ph)—CO2H | " | H |
| 198 | " | " | " | H | —NHCOC(Ph)=C(Ph)—CO2H | " |
| 199 | " | " | " | " | H | —NHCOC(Ph)=C(Ph)—CO2H |
| 200 | HS | H | CH2OH | " | " | NO2 |
| 201 | H | " | " | " | " | " |
| 202 | n-Bu | Cl | CH2OMe | " | " | CO2Me |
| 203 | " | " | " | " | " | CO2H |
| 204 | Et | " | CH2CO2H | " | " | H |
| 205 | i-Pr | " | " | " | " | " |
| 206 | n-Bu | " | " | " | " | " |
| 207 | " | " | " | Cl | " | " |
| 208 | " | " | " | NO2 | " | " |
| 209 | n-Pr | " | " | H | " | " |
| 210 | i-Bu | Cl | CH2CO2H | H | H | H |
| 211 | n-Pen | " | " | " | " | " |
| 212 | " | " | " | Cl | " | " |
| 213 | n-Hex | " | " | " | " | " |
| 214 | c-Pen | " | " | H | " | " |
| 215 | c-Hex | " | " | " | " | " |
| 216 | n-Bu | " | " | " | " | n-Bu—O |
| 217 | Ph— | " | " | Cl | " | H |
| 218 | " | " | " | H | " | n-Bu—O |
| 219 | n-Bu | " | " | Cl | Me | H |
| 220 | " | " | " | H | " | MeO |
| 221 | n-Hex | " | " | " | " | " |
| 222 | Ph | " | " | " | " | EtO |
| 223 | n-Bu | " | " | " | " | MeO |
| 224 | n-Hex | " | " | " | " | " |
| 225 | Ph | " | " | " | " | HO |
| 226 | " | " | " | " | H | " |
| 227 | " | " | " | " | Me | MeCOO |
| 228 | " | " | " | " | " | n-Bu—O |
| 229 | " | " | " | " | " | MeO |
| 230 | " | " | " | MeO | H | H |
| 231 | " | " | " | H | MeO | " |
| 232 | " | " | " | " | H | MeO |
| 233 | " | " | " | " | " | EtO |
| 234 | Ph | Cl | CH2CO2H | H | H | n-Bu—O |
| 235 | " | " | " | " | " | PhCH2O |
| 236 | " | " | " | " | MeO | MeO |
| 237 | " | " | " | " | Me | " |
| 238 | Me | " | " | " | H | H |
| 239 | n-Bu | " | CH2CONH2 | " | " | " |
| 240 | " | CH2COOH | Cl | Cl | " | " |
| 241 | Ph | Cl | CH2CO2H | H | " | Me |
| 242 | " | " | " | Me | " | H |
| 243 | " | " | " | H | " | Cl |
| 244 | " | " | " | Cl | " | H |
| 245 | " | " | " | " | " | Cl |
| 246 | " | " | " | Br | " | " |
| 247 | " | " | " | F | " | " |
| 248 | " | Cl | " | H | " | " |
| 249 | " | Br | " | " | " | " |

TABLE 2-continued

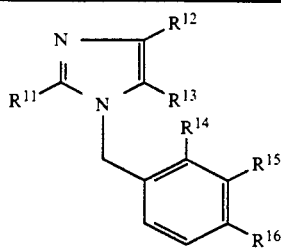

| No. | $R^{11}$ | $R^{12}$ | $R^{13}$ | $R^{14}$ | $R^{15}$ | $R^{16}$ |
|---|---|---|---|---|---|---|
| 250 | (2-thienyl) | Cl | " | " | " | " |
| 251 | Ph | " | $CH_2CO_2Et$ | " | " | " |
| 252 | " | " | $CH_2CO_2H$ | " | " | $NH_2$ |
| 253 | " | $CH_2CO_2H$ | Cl | " | " | H |
| 254 | " | Cl | $CO_2H$ | " | " | " |
| 255 | " | " | $(CH_2)_2CO_2H$ | " | " | " |
| 256 | c-Pen | $CH_2CO_2H$ | Cl | " | " | " |
| 257 | Ph | Cl | $CH_2CONH_2$ | " | " | " |

TABLE 3

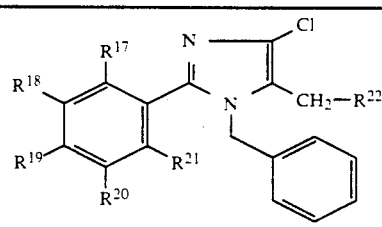

| No. | $R^{17}$ | $R^{18}$ | $R^{19}$ | $R^{20}$ | $R^{21}$ | $R^{22}$ |
|---|---|---|---|---|---|---|
| 258 | H | H | Me | H | H | $CO_2H$ |
| 259 | " | " | MeO | " | " | " |
| 260 | " | " | n-BuNH | " | " | " |
| 261 | $NO_2$ | " | H | " | " | " |
| 262 | H | " | $NH_2$ | " | " | " |
| 263 | $NH_2$ | " | H | " | " | " |
| 264 | H | " | HO | " | " | " |
| 265 | " | HO | H | " | " | " |
| 266 | HO | H | " | " | " | " |
| 267 | H | $NO_2$ | $Me_2N$ | " | " | " |
| 268 | " | " | " | $NO_2$ | " | " |
| 269 | " | " | Cl | " | " | " |
| 270 | " | H | $Me_2N$ | H | " | " |

TABLE 3-continued

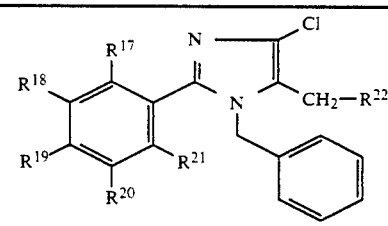

| No. | $R^{17}$ | $R^{18}$ | $R^{19}$ | $R^{20}$ | $R^{21}$ | $R^{22}$ |
|---|---|---|---|---|---|---|
| 271 | " | MeO | H | " | " | " |
| 272 | " | H | n-BuO | " | " | " |
| 273 | " | " | i-Pr | " | " | " |
| 274 | " | " | $Me_2N$ | " | " | $CONH_2$ |
| 275 | " | Cl | $Et_2N$ | " | " | $CO_2H$ |
| 276 | " | " | $Me_2N$ | " | " | " |
| 277 | " | Br | " | " | " | " |
| 278 | " | HO | HO | " | " | " |
| 279 | H | MeO | H | H | H | $CO_2H$ |
| 280 | " | " | HO | " | " | " |
| 281 | " | " | MeO | " | " | " |
| 282 | " | Me | " | " | " | " |
| 283 | " | MeO | $PhCH_2O$ | " | " | " |

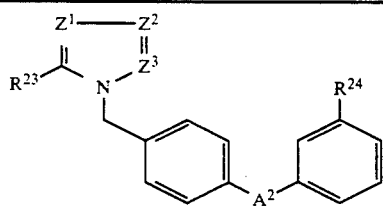

| No. | $R^{23}$ | $Z^1$ | $Z^2$ | $Z^3$ | $A^2$ | $R^{24}$ |
|---|---|---|---|---|---|---|
| 284 | H | C-n-Bu | N | N | single bond | $CO_2H$ |
| 285 | n-Bu | CH | " | " | " | " |
| 286 | " | " | " | " | " | Tet |
| 287 | H | C-n-Bu | " | " | " | " |
| 288 | " | C-Et | " | " | " | $CO_2H$ |
| 289 | Et | CH | " | " | " | " |
| 290 | H | C-n-Pr | " | " | " | " |
| 291 | n-Pr | " | " | " | " | " |
| 292 | H | C-n-Pen | " | " | —CO— | " |
| 293 | n-Pen | CH | " | " | " | " |

-continued

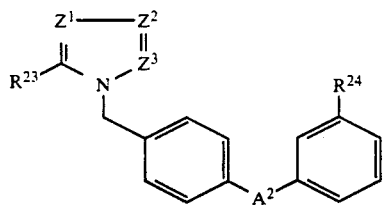

| No. | R²³ | Z¹ | Z² | Z³ | A² | R²⁴ |
|---|---|---|---|---|---|---|
| 294 | n-Bu | N | " | C—CH₂OMe | single bond | " |
| 295 | " | " | " | CH | " | " |
| 296 | n-Pr | " | " | C—CH₂OMe | " | " |
| 297 | Et | " | " | " | " | " |
| 298 | n-Bu | " | " | C-n-Bu | " | " |
| 299 | n-Pr | " | " | C—CH₂OMe | " | " |
| 300 | CH₂OMe | CH | C-n-Bu | N | " | " |
| 301 | n-Bu | " | C—CH₂OMe | " | " | " |
| 302 | —(CH₂)₂CH=CH₂ | " | " | " | " | " |
| 303 | n-Pr | " | " | " | " | " |
| 304 | CH₂OMe | " | C-n-Pr | " | " | " |
| 305 | n-Pr | CH | C—COOH | N | single bond | CO₂H |
| 306 | " | " | C-CH₂OH | " | " | " |
| 307 | CH₂OH | " | C-n-Pr | " | " | " |
| 308 | n-Pr | " | C—CHO | " | " | " |
| 309 | CHO | " | C-n-Pr | " | " | " |
| 310 | n-Pr | " | CH | C—CO₂Et | " | Tet |
| 311 | " | " | " | " | " | CO₂H |
| 312 | " | " | " | C—CO₂H | " | " |
| 313 | " | " | " | C—CHO | " | " |
| 314 | n-Bu | " | " | C—CO₂Et | " | Tet |
| 315 | " | " | " | C—CO₂H | " | " |
| 316 | n-Pr | " | " | C—CHO | " | " |

TABLE 5

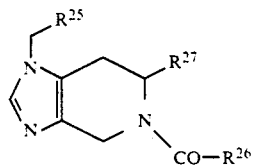

| No. | R²⁵ | R²⁶ | R²⁷ |
|---|---|---|---|
| 317 | Ph | CHPh₂ | CO₂H |
| 318 | " | CH(—C₆H₄—Cl)₂ | " |
| 319 | " | 9-fluorenyl (CH) | " |
| 320 | 2-Me-4-aminophenyl | CHPh₂ | " |
| 321 | Ph | N(Me)(Ph) | CH₂OH |

TABLE 5-continued
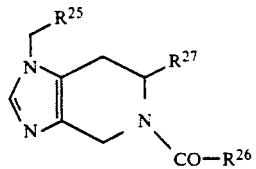
| No. | R²⁵ | R²⁶ | R²⁷ |
|---|---|---|---|
| 322 | 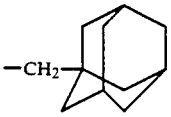 -CH₂- (adamantyl) | CH₂Ph₂ | CO₂H |
| 323 | 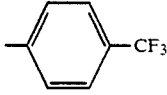 -C₆H₄-CF₃ | " | " |
| 324 | —CH₂—C—Hex | " | " |
| 325 | 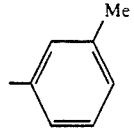 3-Me-C₆H₄- | " | " |
| 326 | 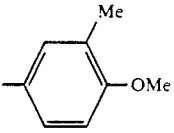 2-Me-4-OMe-C₆H₃- | " | CH₂OH |
| 327 | 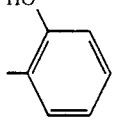 2-HO-C₆H₄- | " | CO₂H |
| 328 | 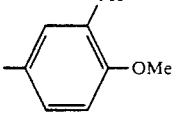 2-Me-4-OMe-C₆H₃- | CH(c-Hex)(Ph) | " |
| 329 | " | CH₂-c-Hex | " |
| 330 | " | CHPh₂ | " |
| 331 | " | 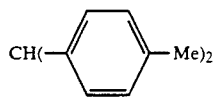 CH(-C₆H₄-Me)₂ | " |
| 332 | CH₂Ph | CHPh₂ | " |
| 333 | Ph | 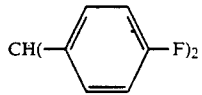 CH(-C₆H₄-F)₂ | " |

TABLE 6
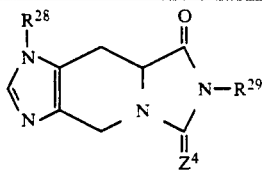
| No. | $R^{28}$ | $R^{29}$ | $Z^4$ |
|---|---|---|---|
| 334 | H | 4-SMe-C6H4 | O |
| 335 | " | 4-OMe-C6H4 | " |
| 336 | " | 3,4-(OMe)2-C6H3 | " |
| 337 | " | i-Pr | " |
| 338 | " | t-Bu | " |
| 339 | " | i-Pr | S |
| 340 | " | Pr | " |
| 341 | " | 4-OMe-C6H4 | " |
TABLE 6-continued
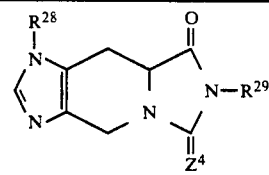
| No. | $R^{28}$ | $R^{29}$ | $Z^4$ |
|---|---|---|---|
| 342 | " | 4-NMe2-C6H4 | " |
| 343 | CH2Ph | i-Pr | O |
| 344 | " | 4-OMe-C6H4 | S |
| 345 | " | " | O |
| 346 | " | 3-Me-4-OMe-C6H3-CH2 | S |
| 347 | " | " | O |
compound 348
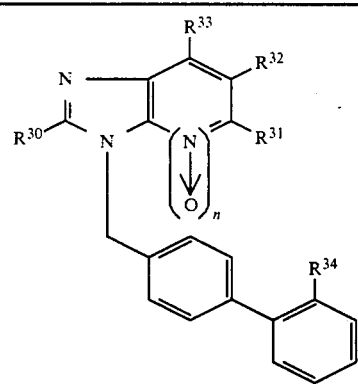
TABLE 7
| No. | $R^{30}$ | $R^{31}$ | $R^{32}$ | $R^{33}$ | $R^{34}$ | n |
|---|---|---|---|---|---|---|
| 349 | n-Bu | H | H | H | CO2H | 0 |
| 350 | " | " | " | " | Tet | " |
| 351 | n-Pr | " | " | " | " | " |
| 352 | " | " | " | Me | " | " |
| 353 | n-Bu | " | " | " | " | " |
| 354 | Et | Me | " | " | " | " |
| 355 | n-Pr | " | " | " | " | " |
| 356 | n-Bu | " | " | " | " | " |
| 357 | Et | " | " | " | CO2H | " |
| 358 | n-Pr | NH2 | " | H | Tet | " |
| 359 | Et | H | " | Me | " | " |
| 360 | Me | " | " | " | " | " |
| 361 | n-Pen | " | " | " | " | " |

TABLE 7-continued

| No. | R³⁰ | R³¹ | R³² | R³³ | R³⁴ | n |
|---|---|---|---|---|---|---|
| 362 | n-Non | " | " | " | " | " |
| 363 | i-Pr | " | " | " | " | " |
| 364 | i-Bu | " | " | " | " | " |
| 365 | c-Pr | " | " | " | " | " |
| 366 | MeOCH₂ | " | " | " | " | " |
| 367 | n-Pr | " | " | " | CO₂H | " |
| 368 | " | " | " | " | CONHSO₂Ph | " |
| 369 | n-Pr | H | H | Me | CONHSO₂-（4-Cl-C₆H₄） | 0 |
| 370 | " | " | " | " | CONHSO₂Me | " |
| 371 | c-Pr | Me | " | " | Tet | " |
| 372 | " | " | n-Pr | " | " | " |
| 373 | n-Pr | H | H | " | CONHSO₂CF₃ | " |
| 374 | Et | Me | " | " | NO₂ | " |
| 375 | n-Pr | H | " | " | CH₂SO₂NHCOMe | " |
| 376 | Et | Br | " | " | Tet | " |
| 377 | " | Cl | " | " | " | " |
| 378 | " | CN | " | " | " | " |
| 379 | " | CO₂H | " | " | " | " |
| 380 | " | CO₂Et | " | " | " | " |
| 381 | " | CO₂Me | " | " | " | " |
| 382 | " | CO₂CH₂Ph | " | " | " | " |
| 383 | " | CO₂i-Pr | " | " | " | " |
| 384 | " | CO₂n-Bu | " | " | " | " |
| 385 | " | CONH₂ | " | " | " | " |
| 386 | " | morpholino (N⌒O) | " | " | " | " |
| 387 | " | i-Pr | " | " | " | " |
| 388 | " | Et | " | " | " | " |
| 389 | " | n-Hex | " | " | " | " |
| 390 | " | Ph | " | " | " | " |
| 391 | " | Tet | " | " | " | " |
| 392 | " | COMe | " | " | " | " |
| 393 | " | MeCHOH-(RS) | " | " | " | " |
| 394 | " | CH₂OH | " | " | " | " |
| 395 | Et | CH₂CH(OH)Me | H | Me | Tet | 0 |
| 396 | " | C(OH)Et₂ | " | " | " | " |
| 397 | " | NH₂ | " | " | " | " |
| 398 | " | " | " | CF₃ | " | " |
| 399 | " | NHMe | " | Me | " | " |
| 400 | " | NHMe₂ | " | " | " | " |
| 401 | n-Pr | " | " | H | " | " |
| 402 | Et | NHn-Hex | " | Me | " | " |
| 403 | " | NH(CH₂)₂NH₂ | " | " | " | " |
| 404 | " | CH₂CO₂H | " | " | " | " |
| 405 | " | morpholino (N⌒O) | " | " | " | " |

TABLE 7-continued

| No. | $R^{30}$ | $R^{31}$ | $R^{32}$ | $R^{33}$ | $R^{34}$ | n |
|-----|----------|----------|----------|----------|----------|---|
| 406 | " | SMe | " | " | " | " |
| 407 | " | OH | " | " | " | " |
| 408 | " | OEt | " | " | " | " |
| 409 | " | (CH$_2$)$_2$NHCOMe | " | " | " | " |
| 410 | " | Me | " | H | " | " |
| 411 | n-Pr | " | " | " | " | " |
| 412 | " | " | Me | " | " | " |
| 413 | " | H | Br | Me | " | " |
| 414 | " | " | H | Et | " | " |
| 415 | " | " | " | i-Pr | " | " |
| 416 | Et | " | " | Et | " | " |
| 417 | n-Pr | " | CH$_2$OH | Me | " | " |
| 418 | " | " | H | -C$_6$H$_4$-Me (p) | " | " |
| 419 | " | " | -C$_6$H$_4$-Me (p) | Me | " | " |
| 420 | " | Cl | H | H | " | " |
| 421 | n-Pr | Me | NH$_2$ | Me | Tet | 0 |
| 422 | " | H | H | " | " | 1 |
| 423 | " | Me | OH | " | " | 0 |
| 424 | CF$_3$CH(Me) | " | H | " | " | " |
| 425 | HC≡C(CH$_2$)$_2$ | " | " | " | " | " |
| 426 | Me | " | " | " | " | " |
| 427 | Et | " | " | Cl | " | " |
| 428 | " | " | " | morpholino | " | " |
| 429 | " | " | " | NHMe | " | " |
| 430 | " | " | " | NMe$_2$ | " | " |
| 431 | " | " | " | SMe | " | " |
| 432 | " | CH$_2$OCOMe | " | Me | " | " |

TABLE 8

| No. | $R^{35}$ | $R^{36}$ | $R^{37}$ |
|---|---|---|---|
| 433 | (1,4-dimethyl-2-ethyl-imidazo[4,5-b]pyridin-3-yl) | Cl | Tet |
| 434 | " | F | " |
| 435 | (1-methyl-2-n-butyl-imidazo[4,5-b]pyridin-3-yl) | H | $CO_2H$ |
| 436 | (1-methyl-2-n-butyl-imidazo[4,5-c]pyridin-3-yl) | " | " |
| 437 | (1-methyl-2-n-butyl-imidazo[4,5-d]pyridin-3-yl) | " | " |

TABLE 9

| No. | $R^{38}$ | $R^{39}$ | $R^{40}$ | $R^{41}$ |
|---|---|---|---|---|
| 438 | H | Cl | n-Pr | $CO_2H$ |
| 439 | " | " | n-Bu | " |
| 440 | " | H | " | " |
| 441 | " | Cl | n-Pr | Tet |
| 442 | " | H | " | " |
| 443 | " | Cl | n-Bu | " |
| 444 | " | H | " | " |
| 445 | Cl | Me | n-Pr | " |
| 446 | $Me_2N$ | " | " | " |
| 447 | MeNH | " | " | " |
| 448 | morpholino | " | " | " | compound 449 (1,3-dimethyl-2-n-butyl-xanthine linked via imidazole N to 4'-(2-(1H-tetrazol-5-yl)phenyl)benzyl)

TABLE 10

| No. | $R^{42}$ | $R^{43}$ | $R^{44}$ | $R^{45}$ | $R^{46}$ |
|---|---|---|---|---|---|
| 450 | n-Bu | 2-($CO_2Me$)benzyl | OMe | H | H |
| 451 | " | " | H | OMe | " |
| 452 | " | " | $CH_2OH$ | H | " |
| 453 | " | " | H | $CH_2OH$ | " |

TABLE 10-continued

[Structure: benzimidazole with R42, R43, R44, R45, R46 substituents]

| No. | R42 | R43 | R44 | R45 | R46 |
|---|---|---|---|---|---|
| 453 | " | —NHCO-(2-NHSO$_2$CF$_3$-phenyl) | " | H | (CH$_2$)$_2$CO$_2$Et |
| 454 | CH=CHCO$_2$Et | NH$_2$ | " | " | H |
| 455 | " | NO$_2$ | " | " | " |
| 456 | CH=CH-n-Pr | NH$_2$ | " | " | " |
| 457 | " | NO$_2$ | " | " | " |
| 458 | CHO | " | " | " | " |
| 459 | (CH$_2$)$_2$CO$_2$Et | " | " | " | " |
| 460 | (CH$_2$)$_2$CO$_2$H | " | " | " | " |
| 461 | CH$_2$CH(CO$_2$Et)$_2$ | " | " | " | " |
| 462 | " | NH$_2$ | " | " | " |
| 463 | CH$_2$Cl | NO$_2$ | " | " | " |
| 463 | CH$_2$OH | " | " | " | " |
| 464 | n-Bu | —NHCO-(2-CO$_2$H-phenyl) | " | Cl | " |

Abbreviations used in this specification and claims are given below.

Tet: tetrazol-5-yl

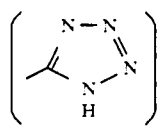

Tet.K: a group shown by formula:

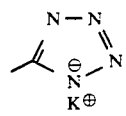

o-CP: 2-carboxyphenyl:

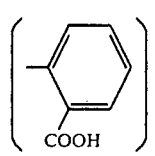

p-MP: 4-methoxyphenyl

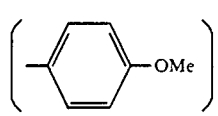

Ph: phenyl

Me: methyl

Et: ethyl n-Pr: n-propyl i-Pr: isopropyl c-Pr: cyclopropyl n-Bu: n-butyl i-Bu: isobutyl t-Bu: tert-butyl n-Pen: n-pentyl c-Pen: cyclopentyl n-Hex: n-hexyl c-Hex: cyclohexyl n-Non: n-nonyl L—Pro or D—Pro: L-prolyl or D-prolyl L—Phe or D—Phe: L-phenylalanyl or D-phenylalanyl The symbol " at each column means the same as the description at the column right above.

The non-peptide type antiotensin II receptor antagonist itself which is used in the present invention can be prepared and obtained by any one of the processes described in publications (a) through (o) and the patents (1) through (12) supra.

Next, the present invention is described more specifically, with reference to test examples.

TEST EXAMPLE

Uric acid excretion activity

Twenty-four (24) male adults (25 to 48 years old, 161 cm to 187 cm tall, weighing 48 kg to 85 kg) were divided into 4 groups, 6 per group. Compound No. 9 was orally administered under hunger in the form of capsules in Example 2, in a definite dose (25 mg, 50 mg, 100 mg or 200 mg) per person, by varying the dose in each group. Further in order to examine influence of diet on uric acid excretion increasing activity of Compound No. 9, the capsule of Example 2 containing 100 mg of Compound No. 9 was orally administered at 2 weeks after the test under hunger was completed. Concentration of uric acid in urine and blood was determined by the uricase-POD method at every definite period of time after the administration. The results are shown in Tables 11 through 14.

As is clear from Tables 11 through 14, the concentration of uric acid in serum decreased in 4 hours after medication dose-dependently. However, a tendency that the uric acid concentration was recovered to the concentration level prior to medication was noted 24 hours after. On the other hand, when medicated after meals, the concentration of uric acid in serum was kept as it decreased even 24 hours after.

The uric acid concentration in urine dose-dependently increased from 0 to 4 hours by administering Compound no. 9 in doses of 25 mg, 50 mg and 100 mg per person. In the dose of 200 mg, however, the uric acid concentration in urine did not increase dose-dependently but was kept almost constant. On the other hand, when medicated after meals, the uric acid concentration in urine increased in 0 to 8 hours.

The foregoing results reveal that the non-peptide type compounds having an angiotensin II receptor-antagonizing activity in accordance with the present invention have the activities of reducing the uric acid concentration in blood and increasing excretion of uric acid into urine. Accordingly, the non-peptide type compounds having an angiotensin II receptor-antagonizing activity in accordance with the present invention are useful as drugs for the prevention or treatment of hyperuricemia.

TABLE 11

Change of uric acid concentration in serum with passage of time when administered in hunger

| Time (hr) | Dose (mg/man) Concentration of Uric Acid (mg/dl) | | | |
|---|---|---|---|---|
| | 25 | 50 | 100 | 200 |
| 0 (when administerd) | 5.2 ± 0.5 | 6.1 ± 1.4 | 5.9 ± 0.9 | 5.6 ± 0.7 |
| 4 | 4.8 ± 0.6 | 5.3 ± 1.3 | 4.6 ± 0.7 | 4.3 ± 0.9 |
| 24 | 4.6 ± 0.6 | 5.6 ± 1.4 | 5.2 ± 0.8 | 5.0 ± 0.9 |

TABLE 12

Change in uric acid concentration in serum with passage of time after meal

| Time (hr) | Dose (mg/man) Concentration of Uric Acid (mg/hr) |
|---|---|
| | 100 |
| 0 (when administerd) | 5.8 ± 1.1 |
| 4 | 4.9 ± 1.0 |
| 24 | 4.7 ± 0.9 |

TABLE 13

Change in uric acid excretion in urine with passage of time when administered in hunger

| Time (hr) | Dose (mg/man) Concentration of Uric Acid (mg/hr) | | | |
|---|---|---|---|---|
| | 25 | 50 | 100 | 200 |
| 0-4 | 43.0 ± 24.5 | 52.8 ± 4.3 | 81.2 ± 15.7 | 78.7 ± 15.3 |
| 4-8 | 32.4 ± 14.7 | 42.9 ± 8.5 | 36.4 ± 7.7 | 25.4 ± 6.6 |
| 8-12 | 28.7 ± 13.6 | 39.1 ± 4.4 | 30.1 ± 6.8 | 19.6 ± 5.2 |
| 12-24 | 19.7 ± 9.9 | 22.2 ± 3.8 | 19.2 ± 4.2 | 13.4 ± 2.3 |
| 24-40 | 33.2 ± 21.9 | 26.6 ± 5.4 | 28.0 ± 7.2 | 21.0 ± 3.0 |

TABLE 14

Change of uric acid excretion in urine with passage of time after meal

| Time (hr) | Dose (mg/man) Concentration of Uric Acid (mg/hr) |
|---|---|
| | 100 |
| 0-4 | 75.9 ± 19.0 |
| 4-8 | 59.0 ± 3.8 |
| 8-12 | 31.8 ± 4.5 |
| 12-24 | 18.9 ± 2.5 |
| 24-30 | 29.5 ± 4.1 |

Where the non-peptide type compounds having an angiotensin II receptor-antagonizing activity in accordance with the present invention are used as compositions for the prevention or treatment of hyperuricemia, the non-peptide type compounds having an angiotensin II receptor-antagonizing activity may be used singly or in the form of pharmaceutical compositions comprising the antagonists and pharmaceutically acceptable carriers.

For preparing the pharmaceutical compositions from the compounds of the present invention, inert and pharmaceutically acceptable carriers may be solid or liquid. The composition in the solid form include powders, tablets, dispersible granules, capsules, cachets and suppositories. The solid carrier may be one or more substances which can also act as a diluent, a flavor, a solubilizing agent, a lubricant, a suspending agent, a binder or a tablet disintegrator. The solid carrier may also be an encapsulated substance. In powder, the carrier is a finely divided solid which is mixed with the active compound. In a tablet, the active compound is mixed with a carrier having a required binding property in an appropriate proportion and the resulting mixture is compressed into a desired shape and size. The powder and tablet contain preferably 5 or 10 to about 70% of the active compound. Suitable examples of the solid carrier include magnesium carbonate, magnesium stearate, talc, sugar, lactose, pectin, dextrin, starch, gelatin, colloidal silicon dioxide, tragacanth gum, sodium carboxymethylstarch, methylcellulose, fine crystalline cellulose, sodium carboxymethylcellulose, low melting point wax, cacao butter, etc. The term preparing into pharmaceutical preparations is contemplated to mean a formulation of an encapsulating substance as a carrier in which the active compound (using or without using any other carrier) is surrounded by the carrier and as the result, the carrier gives a capsule together with the active compound, and the inactive compound. Likewise, a cachet also falls under the term. The tablet, powder, cachet and capsule may be used as a solid form of application suited for oral administration.

In preparing a suppository, a low melting point wax such as a mixture of fatty acid glycerides or cacaco butter is first allowed to melt and the active compound is uniformly dispersed in the melt by, e.g., stirring. The melted homogeneous mixture is then poured into a mold of suitable size, cooled and solidified.

The preparation of liquid form includes a solution, a suspension and an emulsion. Examples of the liquid carrier are water for parenteral injection or an aqueous propylene glycol solution. The liquid preparation may also be a solution in a polyethylene glycol aqueous solution. The aqueous solution suited for oral application may be prepared by dissolving the active compound in water and, if necessary, adding a suitable coloring agent, a flavor, a stabilizer and a thickener. The aqueous suspension suitable for oral application may be prepared by dispersing the active compound finely divided in water together with a viscous substance, e.g., natural or synthetic rubber, resin, methylcellulose, sodium carboxymethylcellulose and other known suspending agents.

The composition also includes a preparation in a solid form contemplated to be converted into a preparation in a liquid form for oral or parenteral administration just before application. Such a liquid form includes a solution, a suspension and an emulsion. More advantageously, these preparations in a particular solid form may be provided in a single dosage form and used to make a single liquid dosage as it stands. Instead, a sufficient dose of solid may also be provided so as to ensure each liquid dosage in applications several times, by changing to liquid form and then measuring a definite volume of the preparation in a liquid form with a syringe, a teaspoon or other container for determining its volume, etc. In case that liquid dosages to be applied several times are thus provided, it is preferred to maintain the unused portion of the liquid dosage at a low temperature (for example, under cooling). The preparation in a solid form designed to be converted into a liquid form may contain, in addition to the active compound, a flavor, a coloring agent, a stabilizer, a buffer, an artificial and natural sweetner, a dispersing agent, a thickener, a solubilizing agent, etc. The liquid used to prepare the preparation in a liquid form is water, isotonic water, ethanol, glycerine, propylene glycol, etc. and a mixture thereof. The liquid used is generally chosen in association with mode of application. For example, a liquid preparation containing large quantities of ethanol is inappropriate for parenteral application.

It is preferred that the pharmaceutical preparation may be in a single dosage form. In such a form, the preparation may be divided into a single dose containing a suitable dose of the active compound. The mode of application in a single dose may be a packaged form containing a discontinuous amount of the preparation, for example, a packaged tablet, capsule and powders in a vial or an ampule. The mode of application in a single dose may be a capsule, cachet or a tablet per se or may be a suitable number of any of its packaged forms.

An amount of the active compound in the single dosage of the preparation may be varied or controlled in a range of 0.1 to 500 mg, preferably 1 to 100 mg, depending upon specific application and titer of the active compound. If necessary, the composition may also contain other compatible therapeutic agents.

In the aforesaid therapeutic use, a daily dose range used for a patient weighing 70 kg is 0.1 to 150 mg per 1 kg of body weight, preferably 1 to 100 mg per 1 kg of body weight, in the case of oral administration; in the case of parenteral administration, 0.1 to 50 mg, preferably 0.1 to 20 mg, per 1 kg of body weight. However, the dose may be varied depending upon necessity for patient, condition of disease to be treated and compound to be used.

Determination of an adequate dose for a specific circumstance may be within the skill of a prescriber. In general, treatment is initiated with a dose less than the optimum dose of a compound. Then, the dose is gradually increased until the best effect is achieved under the situation. If necessary for the sake of convenience, a daily dose may be divided and portionwise administered.

The present invention is further described by referring to the following examples but is not deemed to be limited to these examples:

EXAMPLES

EXAMPLE 1

Capsule

| Component | Content per Capsule |
| --- | --- |
| Compound No. 353 | 50 mg |
| Lactose | 149 mg |
| Magnesium stearate | 1 mg |

Compound No. 353 was prepared into powders having particle size of 60. Lactose and magnesium stearate, which had been similarly passed through blotting paper having a particle size of 60, were added to the powders followed by mixing for 10 minutes. The kneaded mixture was filled up in No. 1 dry gelatin capsule.

EXAMPLE 2

Capsule

| Component | Content per Capsule |
| --- | --- |
| Compound No. 9 | 50 mg |
| Fine crystalline cellulose | 115 mg |
| Lactose | 75.5 mg |
| Magnesium stearate | 1.50 mg |
| Sodium carboxymethyl starch | 18.0 mg |

Compound No. 9 was prepared into powders having particle size of 60. Fine crystalline cellulose, lactose, magnesium stearate and sodium carboxymethyl starch, which had been similarly passed through blotting paper having a particle size of 60, were added to the powders followed by mixing for 10 minutes. The mixture was filled up in No. 1 dry gelatin capsule. Capsule containing 5 mg or 20 mg of Compound 9 were also prepared in a similar manner.

EXAMPLE 3

Capsule

| Component | Content per Capsule |
|---|---|
| Compound No. 9 | 100 mg |
| Colloidal silicon dioxide | 0.2 mg |
| Magnesium stearate | 5 mg |
| Fine crystalline cellulose | 275 mg |
| Starch | 11 mg |
| Lactose | 98.8 mg |

A table was prepared in a conventional manner so as to contain the above components in a dose unit.

What is claimed is:

1. A method of treating hyperuricemia which comprises the administration to a patient in need of such treatment of a therapeutically effective amount of a non-peptide type compound having an angiotensin II receptor-antagonizing activity.

2. The method as claimed in claim 1, wherein said non-peptide type compound having an angiotensin II receptor-antagonizing activity is a compound represented by general formula (I) described below or a pharmaceutically acceptable non-toxic salt thereof:

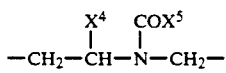

(I)

(wherein each of $Z^1$, $Z^2$ and $Z^3$ independently represents:
nitrogen,
a group represented by general formula: $=C(X^2)-$ or,
a group represented by general formula: $=C(X^3)-$; each or $X^1$, $X^2$ and $X^3$ independently represents:
hydrogen,
hydroxy,
mercapto,
halogen,
formyl,
carboxyl,
carbamoyl,
methoxycarbonyl,
ethoxycarbonyl,
an alkyl group having 1 to 10 carbon atoms (wherein said alkyl group may be substituted with a substituent selected from the group consisting of hydroxy, methoxy, ethoxy, halogen, carboxyl, methoxycarbonyl, ethoxycarbonyl, methoxycarbonylamino, cyano, carbamoyl, acetoxy, acetamido, mercapto, methylthio, ethylthio, phenyl and tetrazolyl), an alkenyl group having 2 to 5 carbon atoms (wherein said alkenyl group may be substituted with a substituent selected from the group consisting of hydroxy, methoxy, ethoxy, carboxyl, methoxycarbonyl and ethoxycarbonyl), an alkynyl having 2 to 5 carbon atoms, a cycloalkyl group having 3 to 6 carbon atoms, an alkoxy group having 1 to 4 carbon atoms, an alkylthio group having 1 to 4 carbon atoms, thienyl, or phenyl (wherein said phenyl may be substituted with 1 to 3 substituents selected from the group consisting of hydroxy, halogen, methoxy, ethoxy, n-propoxy, n-butoxy, mercapto, methylthio, ethylthio, n-propylthio, n-butylthio, methyl, ethyl, n-propyl, isopropyl, n-butyl, nitro, amino, methylamino, dimethylamino, ethylamino, diethylamino, n-propylamino, n-butylamino, phenyl, phenoxy, benzyl, benzyloxy, carboxyl, methoxycarbonyl, ethoxycarbonyl and carbamoyl);

when $Z^2$ and $Z^3$ represent a group represented by general formula: $=C(X^2)-$ or a group represented by general formula: $=C(X^3)-$, $X^2$ and $X^3$ may be combined together to form:

a group represented by general formula:

(wherein $X^4$ represents carboxyl, carbamoyl, formyl, cyano or hydroxymethyl, and, $X^5$ represents fluorenyl, phenyl(methyl)amino, cyclopropylmethyl, cyclopentylmethyl, cyclohexylmethyl, cyclohexyl(phenyl)methyl or benzhydryl: (wherein phenyl in said benzhydryl group may be substituted with a substituent selected from the group consisting of halogen, hydroxy, methoxy, ethoxy, mercapto, methylthio, ethylthio, amino, methylamino, dimethylamino, ethylamino, diethylamino, methyl and ethyl));

a group represented by general formula:

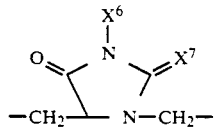

(wherein $X^6$ represents an alkyl group having 1 to 4 carbon atoms or a phenyl:
(wherein said phenyl may be substituted with 1 or 2 substituents selected from the group consisting of halogen, methyl, ethyl, hydroxy, methoxy, ethoxy, mercapto, methylthio, ethylthio, amino, methylamino, dimethylamino, ethylamino and diethylamino); and $X^7$ represents oxygen or sulfur); a group represented by general formula:

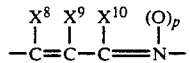

(wherein each of $X^8$, $X^9$ and $X^{10}$ independently represents hydrogen, or alkyl having 1 to 6 carbon atoms):
(wherein said alkyl group may be substituted with hydroxy, amino, mercapto, methoxy, methylthio, carboxyl, carbamoyl, acetylamino or acetoxy); an alkoxycarbonyl having 2 to 5 carbon atoms, halogen, cyano, carboxyl, carbamoyl, acetyl, amino, a mono- or dialkylamino group having 1 to 6 carbon atoms which may by substituted with amino, pyrrolidinyl, piperidino, piperazino, morpholino, thiomorpholino, triazolyl, tetrazolyl, trichloromethyl, tribromomethyl, trifluoromethyl or a phenyl (wherein said phenyl may be substituted with a substituent selected from the group consisting of methyl, ethyl, methoxy, ethoxy, hydroxy, methylthio, ethylthio, mercapto, carboxyl, and cyano); and p represents 0 or 1);

a group represented by general formula;

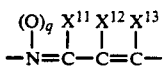

(wherein each of $X^{11}$, $X^{12}$ and $X^{13}$ independently has the same significance as $X^8$, $X^9$ or $X^{10}$, and q has the same significance as p);

a group represented by general formula:

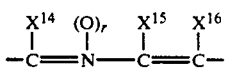

(wherein each of $X^{14}$, $X^{15}$ and $X^{16}$ independently has the same significance as $X^8$, $X^9$ or $X^{10}$, and r has the same significance as p);

a group represented by general formula:

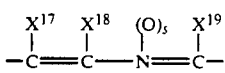

(wherein each of $X^{17}$, $X^{18}$ and $X^{19}$ independently has the same significance as $X^8$, $X^9$ or $X^{10}$, and s has the same significance as p);

a group represented by general formula:

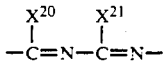

(wherein each of $X^{20}$ and $X^{21}$ independently has the same significance as $X^8$, $X^9$ or $X^{10}$);

a group represented by general formula:

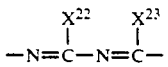

(wherein each of $X^{22}$ and $X^{23}$ independently has the same significance as $X^8$, $X^9$ or $X^{10}$);

a group represented by general formula:

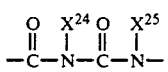

(wherein each of $X^{24}$ and $X^{25}$ independently represents hydrogen or an alkyl group having 1 to 4 carbon atoms (wherein said alkyl group may be substituted with a substituent selected from the group consisting of hydroxy, methoxy, ethoxy, methoxycarbonyl, carboxyl, ethoxycarbonyl and carbamoyl));

a group represented by general formula:

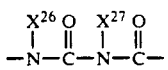

(wherein each of $X^{26}$ and $X^{27}$ independently has the same significance as $X^{24}$ or $X^{25}$); or, a group represented by general formula:

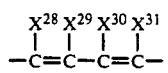

(wherein each of $X^{28}$, $X^{29}$, $X^{30}$ and $X^{31}$ independently represents hydrogen, an alkyl group having 1 to 4 carbon atoms (wherein said alkyl group may be substituted with a substituent selected from the group consisting of hydroxy, methoxy, ethoxy, carboxyl, methoxycarbonyl, ethoxycarbonyl, carbamoyl, acetyl, acetoxy, acetylamino and halogen), a halogen, a perfluoroalkyl group having 1 to 6 carbon atoms, carboxyl, carbamoyl, cyano, formyl, methoxy, ethoxy, propoxy, methoxycarbonyl or ethoxycarbonyl);

Y represents:
phenethyl,
cyclohexylethyl,
adamantylethyl,
or a group represented by formula:

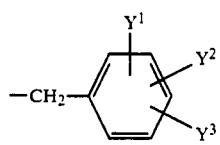

(wherein each of $Y^1$ and $Y^2$ independently represents:
hydrogen,
halogen,
nitro,
carboxyl,
amino,
cyano,
formyl,
hydroxyiminomethyl,
trifluoromethylsulfonylamino,
trifluoroacetylamino,
an alkoxy group having 1 to 4 carbon atoms,
an alkyl group having 1 to 4 carbon atoms,
carboxymethyl, tetrazolylmethyl,
a group represented by formula:

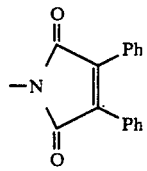

a group represented by formula: —NHCO(CH$_2$)$_t$-COOH (wherein t represents 1 to 3);
a group represented by formula: —NHCOCH=CH—CO$_2$H;
a group represented by formula: —NHCOCH$_2$CH(Ph)CO$_2$H;
a group represented by formula: —NHCOCH(Ph)CH$_2$CO$_2$H;
a group represented by formula:

a group represented by formula:

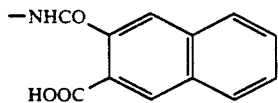

a group represented by formula:

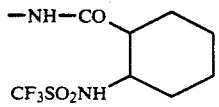

a group represented by formula: —CONHCH(Ph-)CO₂H;
a group represented by formula:

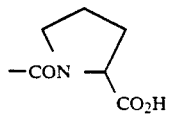

a group represented by formula: —NH-COC(Ph)=C(Ph)CO₂H;
phthalimido;
benzyloxy;
a mono- or dialkylamino having 1 to 4 carbon atoms;
acetoxy; or,
propionyloxy;

$Y^3$ represents:
hydrogen; or,
a group represented by general formula:

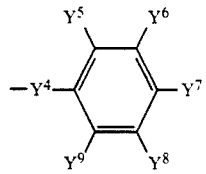

(wherein $Y^4$ represents a single bond; oxygen atom; sulfur atom; carbonyl group;
a group of formula: —NH—;
a group of formula: —CH=CH—
a group of general formula: —N($Y^{10}$)CO—
(wherein $Y^{10}$ represents hydrogen, methyl or phenyl);
a group of general formula: —CON($Y^{11}$)—
(wherein $Y^{11}$ represents hydrogen, methyl or phenyl);
a group of formula: —CH₂NH—;
a group of formula: —NHCH₂—;
a group of general formula: —CH2—$Y^{12}$—
(wherein $Y^{12}$ represents oxygen or sulfur); a group of general formula: —$Y^{13}$—CH₂—
(wherein $Y^{13}$ represents oxygen or sulfur); or,
a group of formula: —NHCONH—;
each of $Y^5$, $Y^6$, $Y^7$, $Y^8$ and $Y^9$ independently represents an alkyl group having 1 to 4 carbon atoms, halogen, carboxyl, carbamoyl, hydroxy, methoxy, ethoxy, mercapto, methylthio, ethylthio, sulfo, sulfamoyl, nitro, trifluoromethanesulfonylamino, methanesulfonylamino, benzenesulfonylamino, 4-chlorobenzenesulfonylamino, acetylaminosulfonylmethy, methoxycarbonyl, ethoxycarbonyl, propyloxycarbonyl, amino, formyl, phospho, phosphono or cyano)).

3. The method of treatment of hyperuricemia as claimed in claim 2, wherein:
$Z^1$ represents nitrogen atom;
$Z^2$ represents a group represented by general formula: —C($X^2$)=;
$Z^3$ represents a group represented by general formula: —C($X^3$)=; and,
Y represents a group represented by general formula:

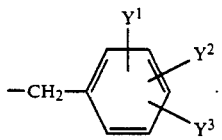

4. The method of treatment of hyperuricemia as claimed in claim 2, wherein:
$Z^1$ represents nitrogen atom;
$Z^2$ represents a group represented by general formula: —C($X^2$)=;
$Z^3$ represents a group represented by general formula: —C($X^3$)+; and $X^2$ and $X^3$ may be combined together to form:
a group represented by general formula:

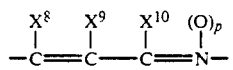

a group represented by general formula:

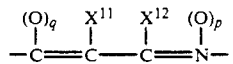

a group represented by general formula:

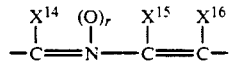

a group represented by general formula:

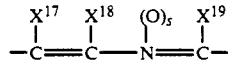

a group represented by general formula:

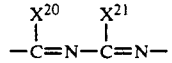

a group represented by general formula:

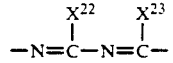

a group represented by general formula: or

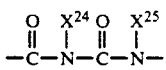

a group represented by general formula:

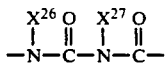

and,
Y represents a group represented by general formula:

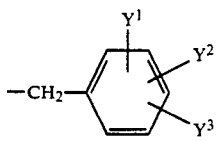

5. The method of treatment of hyperuricemia as claimed in claim 3, wherein $Y^3$ represents a group represented by general formula:

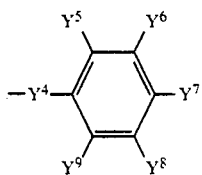

6. The method of treatment of hyperuricemia as claimed in claim 4, wherein $Y^3$ represents a group represented by general formula:

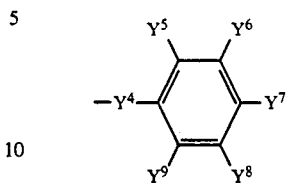

7. The method of treatment of hyperuricemia as claimed in claim 5, wherein $Y^4$ represents a single bond; and $Y^5$ represents carboxyl group or tetrazolyl group.

8. The method of treatment of hyperuricemia as claimed in claim 6, wherein $Y^4$ represents a single bond; and $Y^5$ represents carboxyl group or tetrazolyl group.

9. The method of treatment of hyperuricemia as claimed in claim 2, which is 2-butyl-4-chloro-5-hydroxymethyl-1-[(2'-(1H-tetrazol-5-yl)biphenyl-4-yl)-methyl]imidazole.

10. The method of treatment of hyperuricemia as claimed in claim 2, which is 5,7-dimethyl-2-ethyl-3-[(2'-(1H-tetrazol-5-yl)biphenyl-4-yl)-methyl]-3H-imidazo[4,5-b]pyridine.

11. The method of treatment of hyperuricemia as claimed in claim 2, which is 2-butyl-4-chloro-5-hydroxymethyl-1-[(2'carboxybiphenyl-4-yl)methyl]imidazole.

12. The method of treatment of hyperuricemia as claimed in claim 2, which is 5,7-dimethyl-2-ethyl-3-[(2'carboxybiphenyl-4-yl)methyl]-3H-imidazo[4,5-b]pyridine.

* * * * *